(12) United States Patent
Eistetter

(10) Patent No.: US 6,315,983 B1
(45) Date of Patent: Nov. 13, 2001

(54) PROCESS FOR THE PRODUCTION OF POWDERED PULMONARY SURFACTANT PREPARATIONS

(75) Inventor: Klaus Eistetter, Constance (DE)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/117,142

(22) PCT Filed: Jan. 18, 1997

(86) PCT No.: PCT/EP97/00230

§ 371 Date: Jul. 24, 1998

§ 102(e) Date: Jul. 24, 1998

(87) PCT Pub. No.: WO97/26863

PCT Pub. Date: Jul. 31, 1997

(30) Foreign Application Priority Data

Jan. 24, 1996 (DE) .............................. 196 02 332
Mar. 6, 1996 (EP) .................................. 96103442

(51) Int. Cl.⁷ .................................... A61K 9/127
(52) U.S. Cl. ........................... 424/45; 424/450; 424/489
(58) Field of Search .................... 421/489, 465, 421/1.21, 9.51, 9.52, 450, 45

(56) References Cited

U.S. PATENT DOCUMENTS

| 4,828,844 | | 5/1989 | Röntgen-Odenthal et al. ..... 424/489 |
| 5,658,551 | * | 8/1997 | Schneider et al. .................. 424/9.51 |
| 5,780,014 | | 7/1998 | Eljamal et al. ...................... 424/46 |
| 5,976,574 | * | 1/1999 | Gordon ................................ 424/489 |
| 5,985,248 | * | 11/1999 | Gordon et al. ....................... 424/46 |
| 5,993,783 | | 11/1999 | Eljamal et al. ...................... 424/46 |
| 5,997,848 | | 12/1999 | Patton et al. ........................ 424/46 |
| 6,001,336 | * | 12/1999 | Gordon ................................ 424/46 |
| 6,019,968 | | 2/2000 | Platz et al. ........................ 424/130.1 |
| 6,051,256 | | 4/2000 | Platz et al. .......................... 424/489 |

FOREIGN PATENT DOCUMENTS

| 0 119 056 | | 9/1984 | (EP) . |
| 0 593 094 | | 4/1994 | (EP) . |
| 91/00871 | | 1/1991 | (WO) . |
| 92/06703 | | 4/1992 | (WO) . |
| 92/22315 | | 12/1992 | (WO) . |
| 96/32096 | * | 10/1996 | (WO) . |
| 96/32149 | * | 10/1996 | (WO) . |
| 96/32152 | * | 10/1996 | (WO) . |
| 97/41833 | * | 11/1997 | (WO) . |
| 98/29098 | * | 7/1998 | (WO) . |
| 98/29140 | * | 7/1998 | (WO) . |
| 98/29141 | | 7/1998 | (WO) . |
| 98/29096 | * | 7/1998 | (WO) . |
| 00/00176 | | 1/2000 | (WO) . |
| 00/10541 | | 3/2000 | (WO) . |

* cited by examiner

Primary Examiner—Thurman K. Page
Assistant Examiner—H. Sheikh
(74) Attorney, Agent, or Firm—Jacobson Holman, PLLC

(57) ABSTRACT

A powdered pulmonary surfactant preparation containing a hydrophobic protein serving as a pulmonary surfactant is obtained by spray drying an organic solution or suspension containing a hydrophobic protein serving as a pulmonary surfactant and possibly other components. Obtained power preparations exhibit very good stability under storage, are easy to reconstitute and are also suitable for administration by inhalation.

18 Claims, No Drawings

PROCESS FOR THE PRODUCTION OF POWDERED PULMONARY SURFACTANT PREPARATIONS

TECHINAL FIELD

The invention relates to a process for producing pulverulent pulmonary surfactant preparations.

PRIOR ART

The lungs of all vertebrates contain a substance mixture called "pulmonary surfactant". It has surface-active properties and reduces surface tension in the alveolar region of the lungs to such an extent that collapse of the final regions of the respiratory tract during exhaling is avoided. This substance mixture regulates the surface tension dynamically, so that the collapse of the small alveoli, which is to be expected according to Laplace's law, is avoided in favor of the greater ones, by appropriate adaptation of the surface tension. This results in a well-balanced, histologically and physiologically stable structure of the lung.

Pulmonary surfactant is secreted by the alveolar pneumocytes of type II in the form of lamellar bodies. These are compact units of phospholipid bilayers having a high proportion of dipalmitoylphosphatidylcholine (DPPC) and phosphatidylglycerol (PG). As further essential components, the pulmonary surfactant contains proteins designated SP-A, SP-B and SP-C. SP-A is a high-molecular-weight glycoprotein which plays a decisive role in the regulation of the secretion.

During the formation of the monomolecular surface film (the surfactant in a narrow sense), the hydrophobic proteins SP-C and, to a lesser extent, SP-B play the role of "thermodynamic catalysts". The presence of these proteins accelerates the spreading kinetics enormously. Only because of this, adaptation of the surfactant composition to the prevailing surface tension requirements is possible without delay. These properties are reflected in the extremely hydrophobic character of the proteins, in particular of SP-C.

The lungs of prematurely born babies are not or not sufficiently capable of producing pulmonary surfactant, which leads to life-threatening lack of oxygen (Infant Respiratory Distress Syndrome, IRDS). IRDS is the main cause of death in prematurely born babies.

For many years, IRDS has been treated successfully by introducing pulmonary surfactant preparations into the lungs of the affected children. From pilot studies, it is known that pulmonary surfactant preparations are additionally clinically effective in the case of ARDS (Adult Respiratory Distress Syndrome), including ALI (Acute Lung Injury).

Pulmonary surfactant preparations can be obtained from the lungs of animals by a complicated extraction and centrifugation process (lung lavage), or they can be composed of individual components.

WO 92/06703 describes the production of synthetic pulmonary surfactant preparations by evaporating a chloroform solution comprising phospholipids, such as dipalmitoylphosphatidylcholine (DPPC) and dioleylphosphatidylethanolamine (DOPE), and cholesterol using a rotary evaporator to give a thin film which is resuspended in a buffer, if desired together with suitable proteins.

From WO 91/00871, it is known to concentrate an organic solution of a pulmonary surfactant preparation containing a pulmonary surfactant protein produced by gene technology, to rehydrate it with a buffer and then to lyophilize it. The resulting lyophilizate has the disadvantage that it has to be rehydrated at 37° C. for 15 minutes prior to administration, which is considered by the user to be a very long-winded process prone to errors.

EP 0119056 mentions a process for the production of a pulmonary surfactant preparation where all components are dissolved in an organic solvent, the resulting solution is concentrated to dryness under reduced pressure, the resulting residue is resuspended in an aqueous medium at elevated temperature over a prolonged period of time and the resulting suspension is subjected to freeze-drying. This process is likewise technically very complicated.

DE 3229179 discloses a process for the production of a protein-free pulmonary surfactant preparation where the components are dissolved in glacial acetic acid and the resulting solution is freeze-dried. A disadvantage of this process is the use of glacial acetic acid, since this requires extensive safety precautions.

EP 0655237 proposes the production of drug preparations which are to be administered in the form of a suspension aerosol by inhalation by spray-drying of ethanol/water mixtures. This process is described as being suitable, inter alia, for preparations containing hydrophilic proteins, such as, for example, ecatibant acetate, human insulin and buserelin acetate.

DESCRIPTION OF THE INVENTION

The object on which the present invention is based is to provide a process for the production of protein-containing pulverulent pulmonary surfactant preparations comprising hydrophobic pulmonary surfactant proteins, which is technically as uncomplicated as possible and leads to a storage-stable product which can be used in an advantageous manner.

Surprisingly, it has now been found that this object can be achieved by subjecting an organic solution or suspension containing hydrophobic pulmonary surfactant proteins and, if desired, further components to spray drying.

Using this process, a product is obtained which is storage-stable for a long time and which can be resuspended prior to use without any particular effort. A particular advantage of the resulting powder is its small particle size (1 to 5 $\mu$m) which permits administration by inhalation. This aspect is of particular importance when using pulmonary surfactant preparations as carriers for drugs which are administered via the lungs.

It is very surprising and hitherto unexplainable how the components of pulmonary surfactants, some of which are highly sensitive to temperature, survive the conditions of the spray drying process. Thus, it is known, for example, that the pulmonary surfactant protein SP-C, at temperatures above −20° C., rapidly forms aggregates and is thus inactivated. However, this protein survives the spray drying process according to the invention without any noticeable decomposition and is then present as a loose powder which can be stored at room temperature.

This invention, accordingly, provides a process wherein an organic solution or suspension comprising hydrophobic pulmonary surfactant proteins and, if desired, further components is subjected to spray drying.

Other subject matters are shown in the patent claims.

Suitable hydrophobic pulmonary surfactant proteins are those of natural origin and equally also proteins which have been prepared synthetically, including by gene technological methods, in particular SP-B and SP-C, and mixtures thereof. Synthetic proteins are to be understood as including those proteins whose amino acid sequence deviates more or less from the amino acid sequence of naturally occurring pulmonary surfactant proteins, including those synthetic proteins whose amino acid sequence is conceived entirely independently with respect to their pulmonary surfactant property, as described, for example, in EP 0593094 and EP 92/22315. These proteins can be isolated, synthesized and purified by known methods.

According to the invention, suitable solvents for preparing an organic solution or suspension are alcohols, such as methanol, ethanol, 1-propanol, 2-propanol, butanols, chlorinated hydrocarbons, such as dichloromethane, chloroform, etc., acetone, ethers, hydrocarbons, benzene, toluene and mixtures thereof, it also being possible for the solvents to contain water if they are miscible with water. The maximum water content is 25% by weight. Preference is given to a water content of from 5 to 15% by weight. For the person skilled in the art, it is easy, owing to his skills in the area of spray drying and, if required, by customary experiments, to select the solvents or solvent mixtures which are most suitable for the surfactant mixtures to be dried.

As further components, the pulmonary surfactant preparations contain customary substances, such as, in particular, phospholipids, carboxylic acids and buffer substances.

Prior to spray drying, the solution can be filtered through a sterile filter. Spray drying is carried out in a manner known per se. This technique is described in detail in K. Masters, Spray Drying Handbook, 5th ed. 1991, and in J. Broadhead, S. K. Edmond Ronan, C. T. Rhodes, The Spray Drying of Pharmaceuticals, Drug Dev. Ind. Pharm. 18, 1169 (1992). The principle of spray drying consists of atomizing a solution or suspension of the product to be dried into fine droplets which are dried in a hot gas stream. The solids which remain after the solvent has been evaporated are separated off from the gas stream by means of a cyclone and/or by a filter unit and collected.

According to the invention, it has proven to be advantageous to use as solvents alcohols and chlorinated hydrocarbons, in particular methanol, ethanol, 2-propanol and chloroform and mixtures thereof, if required with a small amount of water (up to a maximum of 25% by weight). Suitable gases for drying are in particular air and nitrogen.

An advantageous gas inlet temperature is from 60 to 200° C., preferably from 90 to 150° C. The gas outlet temperature is maintained, by appropriate control of the spray rate and/or the amount of gas, at from 40 to 80° C., preferably at from 50 to 70° C.

PREPARATION EXAMPLES

Example 1

7.0 g of 1,2-dipalmitoyl-3-sn-phosphatidylcholine, 2,5 g of 1-palmitoyl-2-oleoyl-3-sn-phosphatidylglycerolsodium, 205 mg of calcium chloride dihydrate and 250 mg of palmitic acid are dissolved in 300 ml of ethanol/water (85:15) with heating at 60° C., cooled to room temperature and mixed with 350 ml of a solution of SP-C in chloroform/methanol 9:1 (c=429 mg/l). The resulting solution is spray-dried in a Büchi B 191 lab spray dryer. Spraying conditions: gas for drying air, inlet temperature 90° C., outlet temperature 52–54° C. This gives a loose powder.

Example 2

A solution of surfactant from bovine lungs (obtained by extraction and purification steps, as described, for example, in EP 406732) in chloroform/methanol is spray-dried under the following conditions: Büchi B 191 lab spray dryer, gas for drying nitrogen, inlet temperature 80° C., outlet temperature 50–52° C. This gives a fine yellowish powder.

Example 3

10.95 g of 1,2-dipalmitoyl-3-sn-phosphatidylcholine, 4.6 g of 1-palmitoyl-2-oleoyl-3-sn-phosphatidylglycerolammonium, 418 mg of calcium chloride dihydrate and 750 mg of palmitic acid are dissolved in 330 ml of 2-propanol/water (85:15) at 50° C. and, after cooling to 30° C., are mixed with 620 ml of a solution of SP-C in isopropanol/water (95:5, c=484 mg/l). The resulting solution is spray-dried in a Büchi B 191 lab spray dryer. Spraying conditions: gas for drying nitrogen, inlet temperature 100° C., outlet temperature 58–60° C. This gives a colorless powder.

Example 4

3.74 g (5.1 mmol) of 1,2-dipalmitoyl-3-sn-phosphatidylcholine, 2.81 g (3.7 mmol) of 1-palmitoyl-2-oleoyl-3-sn-phosphatidylcholine, 2.90 g (3.9 mmol) of 1,2-dipalmitoylphosphatidyl-3-sn-phosphatidylglycerol-sodium, 234 mg of palmitic acid and 279 mg (1.9 mmol) of calcium chloride dihydrate are dissolved in 160 ml of 2-propanol/water (85:15) at 50° C and, after cooling to 30° C., are mixed with 566 ml of a solution of SP-C in isopropanol/water (92:8, c=330 mg/l) at 30° C. The resulting solution is spray-dried in a Büchi B 191 lab spray dryer. Spraying conditions: gas for drying nitrogen, inlet temperature 90° C., outlet temperature 58–60° C. This gives a colorless powder.

Example 5

0.5 g of RLLLLRLLLLRLLLLRLLLLR (R=Arg, L=3Leu)7.125 g of 1,2-dipalmitoyl-3-sn-phosphatidylcholine and 2.4 3 g of 1-palmitoyl-2-oleoyl-3-sn-phosphatidylglycerolammonium are dissolved in 500 ml of chloroform/methanol 1:1 with heating at 45° C. and subsequently spray-dried in a Büchi B 191 lab spray dryer. Spraying conditions: gas for drying nitrogen, inlet temperature 85° C., outlet temperature 55° C. This gives a colorless powder.

I claim:

1. A process for producing a pulverulent pulmonary surfactant preparation containing hydrophobic pulmonary surfactant protein which comprises subjecting an organic solution or suspension containing the hydrophobic pulmonary surfactant protein and, optionally, a further component to spray drying.

2. The process as claimed in claim 1, wherein the hydrophobic pulmonary surfactant protein present in the organic solution or suspension is SP-C and/or SP-B.

3. The process as claimed in claim 2, wherein SP-C is present in the organic solution or suspension.

4. The process as claimed in claim 1, wherein the organic solution or suspension contains from 5 to 15% by weight of water.

5. The process as claimed in claim 1, wherein the further component is a phospholipid.

6. The process as claimed in claim 1, wherein the spray drying is carried out in a heated gas.

7. The process as claimed in claim 6, wherein the gas is air or nitrogen.

8. The process as claimed in claim 6, wherein the gas has an inlet temperature of from 60 to 200° C. and an outlet temperature of from 40 to 80° C.

9. The process as claimed in claim 7, wherein the gas has an inlet temperature of from 90 to 150° C. and an outlet temperature of from 50 to 70° C.

10. A pulverulent pulmonary surfactant preparation obtained by a process as claimed in claim 1.

11. A storage-stable protein-containing pulverulent pulmonary surfactant preparation comprising hydrophobic pulmonary surfactant protein in a loose-powder form having a particle size in the range of from 1 to 5 $\mu$m.

12. A preparation as claimed in claim 11 wherein the pulmonary surfactant protein comprises a member selected from the group consisting of SP-C and SP-B.

13. A preparation as claimed in claim 11 further comprising a phospholipid.

14. A preparation as claimed in claim 11 which is easily reconstitutable.

15. A pulverulent pulmonary surfactant preparation as claimed in claim 11 which is essentially the same as a spray-dried organic solution or suspension of the hydrophobic pulmonary surfactant protein.

16. A method of administering a pulmonary surfactant preparation by inhalation to a subject in need of such therapy, wherein the preparation is a preparation as claimed in claim 11.

17. A method of administering a pulmonary surfactant preparation by inhalation to a subject in need of such therapy, wherein the preparation is a preparation as claimed in claim 15.

18. A process as claimed in claim 1, wherein the organic solution or suspension contains up to 25% by weight of water.

* * * * *

SEQUENCE LISTING

<160> NUMBER OF SEQ ID NOS: 1

<210> SEQ ID NO 1
<211> LENGTH: 21

-continued

```
<212> TYPE: PRT
<213> ORGANISM: Artificial Sequence
<220> FEATURE:
<223> OTHER INFORMATION: Description of Artificial Sequence: As
      described in USP 5,260,273

<400> SEQUENCE: 1

Arg Leu Leu Leu Leu Arg Leu Leu Leu Leu Arg Leu Leu Leu Leu Arg
 1               5                  10                  15

Leu Leu Leu Leu Arg
            20
```